United States Patent
Curtis et al.

(10) Patent No.: US 7,772,008 B2
(45) Date of Patent: Aug. 10, 2010

(54) METHOD AND APPARATUS FOR DETERMINING LIQUID VOLUME

(75) Inventors: Richard H. Curtis, Gorham, ME (US);
Ceara J. McNally, Poland, ME (US);
Charles A. Ewing, Westbrook, ME (US)

(73) Assignee: Artel, Inc., Westbrook, ME (US)

( * ) Notice: Subject to any disclaimer, the term of this patent is extended or adjusted under 35 U.S.C. 154(b) by 815 days.

(21) Appl. No.: 11/326,858

(22) Filed: Jan. 6, 2006

(65) Prior Publication Data

US 2007/0161114 A1    Jul. 12, 2007

(51) Int. Cl.
| | |
|---|---|
| G01N 21/00 | (2006.01) |
| B01L 3/00 | (2006.01) |
| G01B 3/00 | (2006.01) |
| G01F 22/00 | (2006.01) |
| G01N 25/20 | (2006.01) |
| G01N 33/50 | (2006.01) |
| G01F 17/00 | (2006.01) |

(52) U.S. Cl. .................. 436/164; 436/147; 422/61; 702/19; 702/25; 702/55; 73/1.73; 73/149

(58) Field of Classification Search ................ 436/147, 436/164; 422/61; 702/19, 25, 55; 73/1.73, 73/149
See application file for complete search history.

(56) References Cited

U.S. PATENT DOCUMENTS

| | | | |
|---|---|---|---|
| 3,492,095 A | 1/1970 | Tillem | |
| 3,565,537 A | 2/1971 | Fielding | |
| 3,705,000 A | 12/1972 | Guerra | |
| 3,737,237 A | 6/1973 | Zurasky | |
| 3,869,211 A | 3/1975 | Watanabe et al. | |
| 3,920,580 A | 11/1975 | Mast | |
| 4,128,339 A | 12/1978 | Yamazaki et al. | |

(Continued)

FOREIGN PATENT DOCUMENTS

EP    0431578 B1    6/1991

(Continued)

OTHER PUBLICATIONS

Cohn et al., "Precision Techniques for Measuring Liquid Quantity," Control Engineering, vol. 15, Jan. 1968, U.S., pp. 51-55 (5 pages).

(Continued)

*Primary Examiner*—Lyle A Alexander
*Assistant Examiner*—Dean Kwak
(74) *Attorney, Agent, or Firm*—Verrill Dana, LLP; Chris A. Caseiro

(57) ABSTRACT

A method, apparatus and kit for precisely and accurately determining the volume of a liquid aliquot which can be used to calibrate a liquid delivery device. Two dye-containing solutions, a sample solution and a diluent solution, are prepared such that each solution contains a different dye, with the solutions having different absorbance values at a first wavelength and at a second wavelength. The absorbance value of a known volume of diluent solution is measured at both wavelengths. Either one aliquot of sample solution is added to the diluent solution and then absorbance measurements are made at both wavelengths, or multiple aliquots of sample solution are mixed serially into the diluent solution and then absorbance measurements are made at both wavelengths after each aliquot is added. The volume of any single aliquot is calculated by using a two-step formula which is based on the Beer-Lambert law.

8 Claims, 4 Drawing Sheets

U.S. PATENT DOCUMENTS

| | | | |
|---|---|---|---|
| 4,248,536 | A | 2/1981 | Hijikata |
| 4,305,659 | A | 12/1981 | Bilstad et al. |
| 4,354,376 | A | 10/1982 | Greenfield et al. |
| 4,357,105 | A | 11/1982 | Liretz |
| 4,405,235 | A | 9/1983 | Rossiter |
| 4,582,684 | A | 4/1986 | Vogel et al. |
| 4,595,561 | A | 6/1986 | Thornton et al. |
| 4,805,623 | A | 2/1989 | Jobsis |
| 5,064,282 | A | 11/1991 | Curtis |
| 5,092,677 | A | 3/1992 | Curtis |
| 5,125,747 | A | 6/1992 | Sayegh et al. |
| 5,244,813 | A | 9/1993 | Walt et al. |
| 5,258,308 | A | 11/1993 | Freeman et al. |
| 5,298,978 | A | 3/1994 | Curtis et al. |
| 5,492,673 | A | 2/1996 | Curtis et al. |
| 5,766,875 | A | 6/1998 | Hafeman et al. |
| 5,959,738 | A | 9/1999 | Hafeman et al. |
| 5,963,318 | A | 10/1999 | Held |
| 6,188,476 | B1 | 2/2001 | Hafeman et al. |
| 6,320,662 | B1 | 11/2001 | Hafeman et al. |
| 6,339,472 | B1 | 1/2002 | Hafeman et al. |
| 6,661,512 | B2 | 12/2003 | Fernando et al. |
| 6,741,365 | B2 | 5/2004 | Curtis |
| 2002/0149772 | A1 | 10/2002 | Halg |
| 2003/0165871 | A1* | 9/2003 | Corson et al. .................. 435/6 |
| 2005/0168737 | A1 | 8/2005 | Bradshaw et al. |

OTHER PUBLICATIONS

Waring et al., "The Chemistry and Application of Dyes," 1990, Plenum Press, New York, U.S., p. 282 (2 pages).

Lubs, "The Chemistry of Synthetic Dyes and Pigments," Amer. Chem. Soc., Color and Chemical Constitution of Dyes, 1970, Hafner Publishing, Darien, CT, US, pp. 675-676 (3 pgs).

International Standard, ISO 8655-7, "Piston-operated volumetric apparatus—Part 7: Non-gravimetric methods for the assessment of equipment performance," Sep. 1, 2005, (27 pgs).

* cited by examiner

METHOD AND APPARATUS FOR DETERMINING LIQUID VOLUME

BACKGROUND OF THE INVENTION

1. Field of the Invention

The present invention relates to a method of determining the volume of an aliquot of a sample solution, and more specifically to a method of determining the volume of an aliquot of a sample solution which involves combining the dye-addition and dye-dilution methods of liquid volume determination, and even more specifically to a method of both precisely and accurately determining the volume of an aliquot of a sample solution.

The present invention also relates to an apparatus for determining the volume of an aliquot of a sample solution, and more specifically to an apparatus for determining the volume of an aliquot of a sample solution which performs part of the method of the present invention, and even more specifically to an apparatus for both precisely and accurately determining the volume of an aliquot of a sample solution.

The present invention also relates to a kit for determining the volume of an aliquot of a sample solution, and more specifically to a kit for determining the volume of an aliquot of a sample solution which involves using the method and apparatus of the present invention, and even more specifically to a kit for both precisely and accurately determining the volume of an aliquot of a sample solution.

Finally, the present invention relates to a method, apparatus, and kit for calibrating a liquid delivery device, such as a pipette, but it is not limited to being used only for that purpose.

2. Description of the Prior Art

Many experimental protocols require use of a small liquid volume, including one of about 5 ml or less. Sometimes this volume must be precisely and accurately known. This is true because in such instances, even a slight error can be deleterious. For example, it is well known in the field of cellular biology that a small discrepancy between the actual and recorded volumes of Bradford reagent used in a small-scale Bradford reaction can significantly skew protein concentration calculation. Where a volume must be precisely and accurately known, it therefore is essential to measure and deliver that volume using a liquid delivery device which has been precisely and accurately calibrated.

Methods and apparatuses which can be used to determine small liquid volumes, and therefore which can be used to calibrate liquid delivery devices, include those which involve spectrophotometric measurement of the light absorbance of a dye-containing liquid sample. For example, U.S. Pat. No. 6,741,365 issued to Curtis (the "Curtis '365 patent"), describes methods and apparatuses for liquid delivery device calibration. The entire contents of the Curtis '365 patent are incorporated herein by reference.

It can be generally stated that there have been only two methods for determining small liquid volumes using spectrophotometry. These methods are referred to as: (1) the dye-addition method, described in the Curtis '365 patent; and (2) the dye-dilution method, which is described in an international standard, ISO 8655 part 7, dated 1 Sep. 2005, which also is incorporated herein by reference. Both of these methods employ a well known relationship entitled the Beer-Lambert Law, according to which the absorbance of light by a dye solution is given by:

$$A = \epsilon_d C_d l \quad (1)$$

where A is the absorbance (dimensionless) of light by the solution at a chosen wavelength, $\epsilon_d$ (cm$^{-1}$ liters/mole) is the extinction coefficient of the dye molecules at that same wavelength (a measure of their ability to absorb light of the wavelength being used for the measurement), $C_d$ (moles/liter) is the concentration of dye molecules in the solution, and l (cm) is the pathlength of light through the solution. Typically, the wavelength of light is chosen to be at or near an absorbance maximum for the dye solution.

According to the dye-addition method, a known volume of diluent solution $V_b$ is put into a measurement vial suitable for making optical measurements. An unknown volume $V_s$ of sample solution containing dye with concentration $C_s$ then is delivered into the known volume of diluent solution. The two solutions are mixed together, and the absorbance of the mixture is measured in a spectrophotometer at a first wavelength $\lambda_s$. The concentration of dye in the resulting mixture is given by:

$$C = C_s \left[ \frac{V_s}{V_b + V_s} \right] \quad (2)$$

From the Beer-Lambert Law and the results of the absorbance measurement, the volume $V_s$ of sample solution that was added is calculated using the formula:

$$V_s = V_b \left[ \frac{A_s}{\varepsilon_s C_s l - A_s} \right] \quad (3)$$

In this method, the absorbance of the mixture $A_s$ is measured at the same wavelength as is the extinction coefficient $\epsilon_s$. In its simplest implementation, only one wavelength of measurement needs to be employed for this method. Typically, the wavelength of measurement $\lambda_s$ is chosen to be at or near the absorbance maximum of the dye.

A variation of this dye-addition method, which is described in the Curtis '365 patent and in U.S. Pat. No. 5,064,282 issued to Curtis, U.S. Pat. No. 5,298,978 issued to Curtis et al., and U.S. Pat. No. 5,492,673 issued to Curtis et al., and pending U.S. Patent Application No. 2005/0168737 by Bradshaw et al., all of which are incorporated herein by reference, requires measurement at a second wavelength $\lambda_b$. In this variant, a dye having an absorbance maximum at $\lambda_b$ is added to the diluent solution, and the concentration $C_b$ of the dye in the diluent solution and the dye's extinction coefficient $\epsilon_b$ are determined or are otherwise obtained. Before any sample solution is added to the diluent solution, the absorbance of the diluent solution $A_b$ is measured at wavelength $\lambda_b$ for the purpose of accurately determining the pathlength l. This marks the only time that absorbance is measured at wavelength $\lambda_b$. When the Beer-Lambert law is applied, the volume of sample solution added is given by:

$$V_s = V_b \left[ \frac{A_s / A_b}{(\varepsilon_s C_s / \varepsilon_b C_b) - (A_s / A_b)} \right] \quad (4)$$

When additional aliquots of sample solution are added to the same vial, volume $V_s(n)$ of the $n^{th}$ such delivery is given by the relationship:

$$V_s(n) = V_T(n-1) \left[ \frac{(A_s(n) - A_s(n-1))/A_b}{(\varepsilon_s C_s / \varepsilon_b C_b) - (A_s(n)/A_b)} \right] \quad (5)$$

In this relationship, $V_T(n-1)$ is the total volume of liquid in the vial after the $n-1^{th}$ delivery, and $V_T(n-1)$ is obtained by adding all the volume calculation results up to and including $V_s(n-1)$ to the initial volume $V_b$. $A_s(n)$ is the absorbance measured at the first wavelength after the $n^{th}$ sample addition.

A significant limitation of the dye-addition method just described is that it tends to be inaccurate when the volume being measured is a significant fraction of the diluent volume $V_b$ (e.g. $V_s \geq \frac{1}{5} V_b$). Indeed, the dye-addition method typically yields multiple volume values which are of similar size to one another (i.e., they are precise), but it does not always yield volume values which reflect the true volume of the sample being tested (i.e., they are not accurate). Due to this limitation, the dye-addition method is not ideally suited for determining large volumes and therefore it also is not ideally suited for calibrating devices which deliver large volumes.

The reason for this limitation is that exact values of the quantities $\varepsilon_s$, $C_s$, $\varepsilon_b$, and $C_b$ must be determined before sample solution can be determined. To the extent that any or all of $\varepsilon_s$, $C_s$, $\varepsilon_b$, and $C_b$ are inexactly known (e.g., due to evaporation or to solution degradation), error will occur in the calculated results. This is especially true in the instance that the volume $V_s$ is an appreciable fraction of the diluent volume $V_b$, since then the denominator in equation (4) is relatively small (the difference between two larger numbers), and is accordingly sensitive to error in either of the two terms in the denominator.

The dye-addition method also is susceptible to "trending", which specifically is a phenomenon whereby volume determination error progressively and cumulatively increases as more and more aliquots of sample solution are added to diluent solution. The volume calculation in equation 5 is the product of the previous volume calculation, which contains error, and a second term with a denominator, which also contains error. This multiplicative error propagation leads to data trending as more and more aliquots are added. For example, when using the dye-addition method to determine the volumes of a series of sample solution volumes, one typically will observe a relatively small level of error, for example, 0.2%, in the volume of a first sample, but see that error level climb significantly higher, for example, to 2%, by the time the volume of a tenth delivery is determined. Indeed, error in data generated by using the dye-addition method can reach a level that some applications will not tolerate after only a few additions of sample solution.

The second of the two methods which involve spectrophotometrically measuring the light absorbance of a liquid sample, the dye-dilution method, is less well known; however, it is described in an international standard, ISO 8655 part 7, dated 1 Sep. 2005, which is incorporated herein by reference. The first step of this method is to add a known amount $V_b$ of solution containing a dye with absorbance maximum at wavelength $\varepsilon_b$ to a vial and then measure the initial absorbance $A_b(i)$ at wavelength $\lambda_b$ of this dye solution. Next, an aliquot of clear liquid solution (e.g., water or buffer) of volume $V_s$ is added, which effectively dilutes the concentration of dye in the original solution, the two solutions are mixed together and a final absorbance $A_b(f)$ is measured. When the Beer-Lambert Law is applied to this method, the volume of sample solution (clear liquid) which was added is given by:

$$V_s = V_b \left[ \frac{A_b(i) - A_b(f)}{A_b(f)} \right] \quad (6)$$

If a series of samples are added to the same vial, the calculated results for the $n^{th}$ addition are:

$$V_s(n) = V_b \left[ \frac{A_b(0)}{A_b(n)} - \frac{A_b(0)}{A_b(n-1)} \right] \quad (7)$$

where $A_b(0)$ is the absorbance measured before any (clear) sample solution is added.

While the dye-dilution method as described above is performed using a sample solution which is clear or, at a minimum, has a coefficient of extinction of zero at the wavelength of measurement, it is not a requirement, provided the coefficient of extinction of the sample solution at the wavelength of measurement is known. The mathematics for such a method can be derived by one skilled in the art.

Unlike the dye-addition method, which tends to be precise but not accurate, the dye-dilution method tends to be accurate but not precise. In other words, by using the dye-dilution method alone, a user likely will obtain a mean volume value which approximates the true volume of an aliquot of a sample solution (i.e., the volume is accurate), but the multiple individual volume values obtained to generate the mean likely will not approximate one another (i.e., they will not be precise). The dye-dilution method tends to be more imprecise when it is used to determine volumes much smaller than $V_b$ (e.g., $\leq \frac{1}{5} V_b$). Increased imprecision at this reduced volume level is attributable to the high relative error in measuring the (relatively small) absorbance differences between $A_b(n)$ and $A_b(n-1)$. While some applications may tolerate such imprecision, others will not. Therefore, since it tends to be imprecise, the dye-dilution method is not ideally suited for determining small volumes, which further means that it also is not ideally suited for calibrating delivery devices which must precisely deliver small volumes.

In light of the above mentioned limitations of the dye-addition and dye-dilution methods, what is needed, therefore, is a system for both precisely and accurately determining the volume of a liquid sample which can be performed and used to precisely and accurately calibrate a liquid delivery device. The system should include one or more of a determination method, an apparatus, and a kit combining an apparatus and instructions for carrying out the method.

SUMMARY OF THE INVENTION

The present invention involves a method, apparatus and kit for precisely and accurately determining the volume of an aliquot of liquid. The invention specifically is a hybrid absorbance volume calculation method, which combines the precision of the dye-addition method of liquid volume determination with the accuracy of the dye-dilution method of liquid volume determination, and also is an apparatus and kit, each of which may be used in whole or in part, to carry out the hybrid absorbance volume calculation method.

The method of the present invention involves making a sample solution by adding a first dye to a solvent at a suitable concentration such that absorbance measurements can be readily made using commonly available spectrophotometric instrumentation. The first dye is chosen so that absorbance values of this sample solution are different at two specified wavelengths $\lambda_s$ and $\lambda_b$. The first dye will typically have, but is not limited to having, an absorbance maximum at wavelength $\lambda_s$, and a lesser value at wavelength $\lambda_b$.

The method continues with preparation of the diluent solution by adding a second dye into a solvent at a suitable concentration such that absorbance measurements may be made. The second dye is chosen so that absorbance values of this diluent solution are different at two specified wavelengths $\lambda_s$ and $\lambda_b$. The second dye will typically have an absorbance maximum at wavelength $\lambda_b$ and a lesser value at wavelength $\lambda_s$.

The method continues with measuring the absorbance values of the diluent solution at wavelength $\lambda_b$ and at wavelength $\lambda_s$ using a spectrophotometer. An aliquot of the sample solution is mixed into the diluent solution and the absorbance values of the mixture of the sample solution and diluent solution are spectrophotometrically measured at wavelength $\lambda_b$ and at wavelength $\lambda_s$. These absorbance values are then used to calculate the precise and accurate volume of the aliquot of sample solution.

In another embodiment of the method, multiple aliquots of sample solution are added serially to the diluent solution after absorbance measurements of the diluent solution are taken at wavelength $\lambda_b$ and at wavelength $\lambda_s$, with each individual aliquot of the multiple aliquots of sample solution being measured both at wavelength $\lambda_b$ and at wavelength $\lambda_s$, prior to the addition the next individual aliquot.

In an embodiment of the apparatus, absorbance data are sent from the spectrophotometer to a central processing unit having computer-executable software. The central processing unit and software then use the absorbance data to calculate the precise and accurate volume of the sample solution using equations described herein.

In an embodiment of the kit, a precisely and accurately measured volume of diluent solution is placed into a liquid holder and the liquid holder is sealed without adding any sample solution. Sealing the diluent solution prior to adding sample solution avoids evaporation and spillage of the diluent solution, which otherwise may occur during shipping of the kit. A sealed diluent solution eliminates a potential source of error in practicing the hybrid absorbance volume calculation method, namely, the mismeasurement of diluent volume by an end-user.

These and other features and advantages of the invention will be apparent upon review of the following detailed description, appended drawings and accompanying claims.

DETAILED DESCRIPTION OF THE PREFERRED EMBODIMENTS OF THE INVENTION

The present invention is a method for precise and accurate determination of the volume of an aliquot of liquid. The method of the present invention is referred to herein as the "hybrid absorbance volume calculation method" 100. The present invention is also a related apparatus and optional kit to aid in performing a portion or all steps of the method described.

Figure 1:
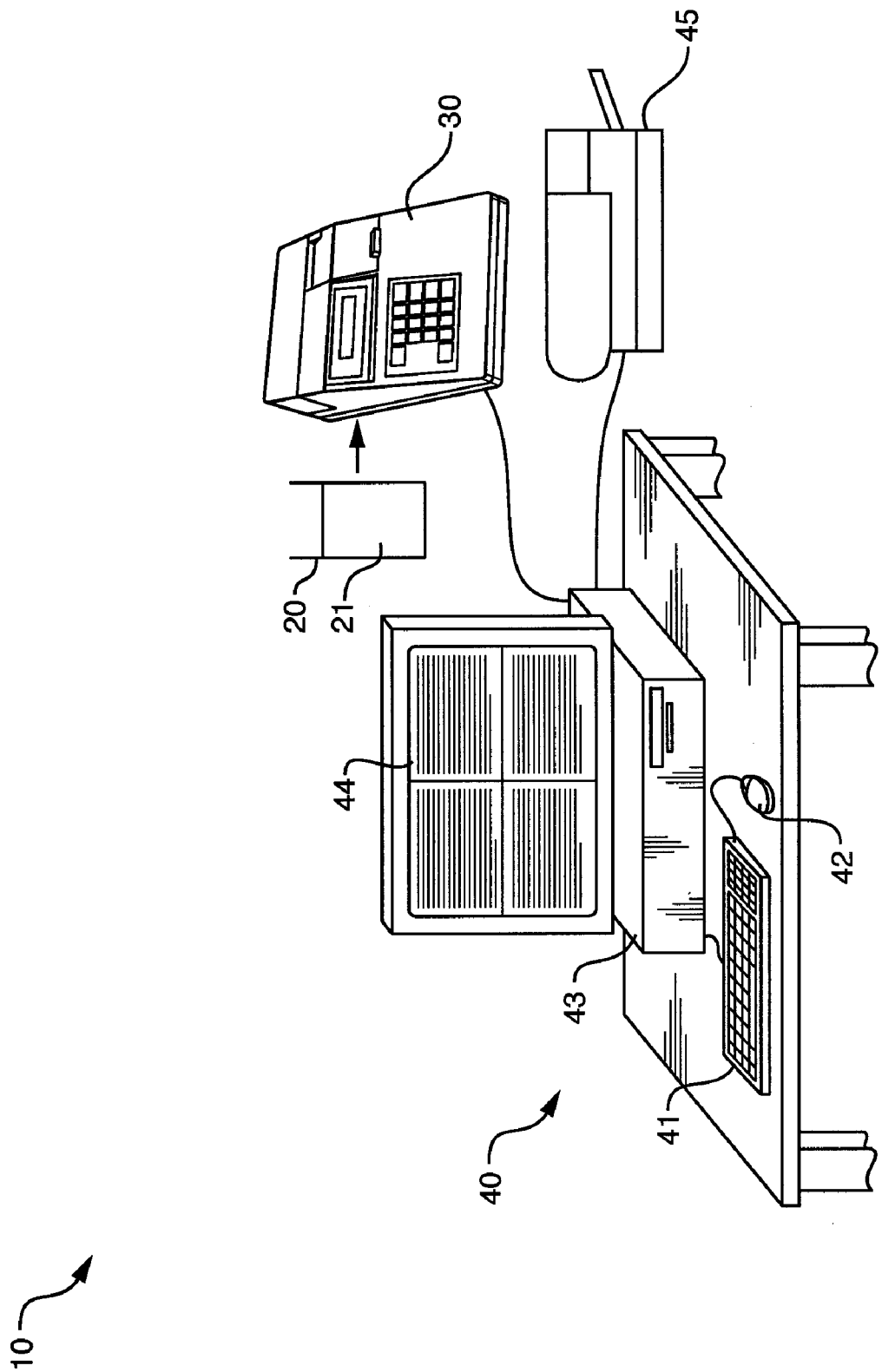
FIG. 1 is a simplified representation of an embodiment of the apparatus including a spectrophotometer and a computing system.

In an embodiment of the apparatus, which is shown in FIG. 1, a volume determining apparatus 10 includes as primary components a liquid holder 20, a spectrophotometer 30, and a computing system 40 capable of carrying out calculations defined through computer-executable software.

In an embodiment of the apparatus, the liquid holder 20 is used to retain the liquid 21 to be analyzed. The liquid holder 20 can be placed into the spectrophotometer 30. The spectrophotometer 30 is capable of being instructed to initiate absorbance measurements on the liquid 21 in the liquid holder 20. These instructions may be carried out through one or more input devices of the spectrophotometer or through the computing system 40. The computing system 40 includes one or more input devices, such as a keyboard 41, a mouse 42, or a combination thereof, which may be used to control the spectrophotometer 30 and/or to perform calculations of volume determination based on the absorbance measurements. The computing system 40, including a computer processor 43 and memory storage, is configured to carry out executable-system instructions for volume determination. Input information and output information may be viewed on a computer display 44. Optionally, a local or remote printer 45 may be employed to print out input information and/or output information.

Figure 2:
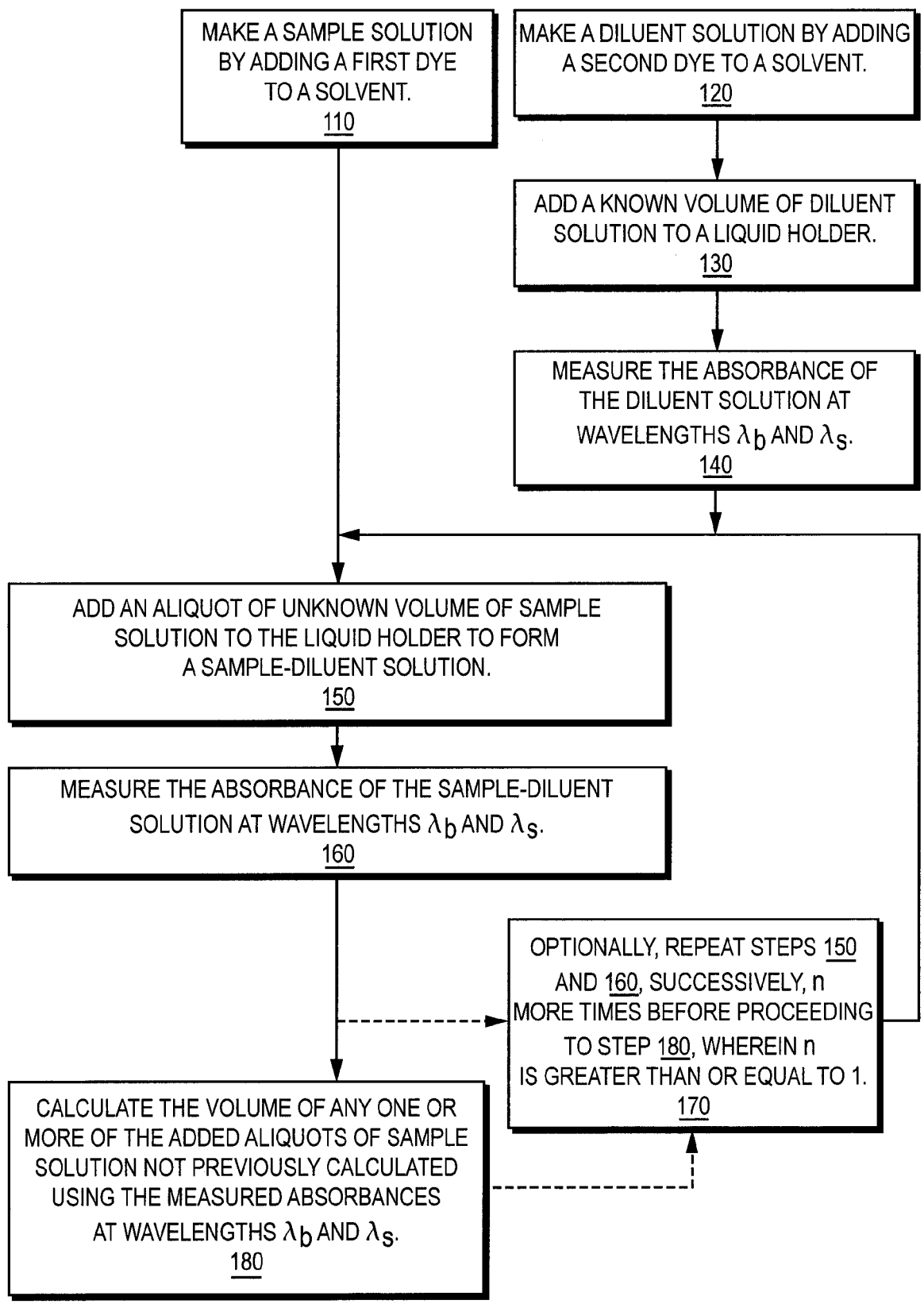
FIG. 2 is a flow diagram showing the steps to be taken for carrying out the preferred embodiments of the hybrid absorbance volume calculation method.

In one preferred embodiment of the hybrid absorbance volume calculation method 100 represented by the steps shown in FIG. 2, a first dye is added to a liquid sample (hereinafter this mixture will be referred to as "the sample solution"), step 110. The first dye in the sample solution has an absorbance value at a first wavelength $\lambda_s$ which is different from the absorbance value of a second dye at the first wavelength $\lambda_s$, and also has an absorbance value at a second wavelength $\lambda_b$ which is different from the absorbance value of the second dye at the second wavelength $\lambda_b$. In a separate mixture, the second dye is mixed into a diluent (hereinafter this mixture will be referred to as "the diluent solution"), step 120. A known volume of diluent solution, $V_b$, is then added to a liquid holder suitable for making absorbance measurements by spectrophotometry, such as liquid holder 20, step 130. Absorbance measurements of the known volume of diluent solution in the liquid holder are made by spectrophotometry at wavelength $\lambda_b$ and at wavelength $\lambda_s$, step 140. Liquid holders suitable for making absorbance measurements by spectrophotometer include those described in the Curtis '365 patent and in the published Bradshaw et al. application. As the next step, a sample solution aliquot of unknown volume, $V_s$, is mixed into the diluent solution in the liquid holder to form a sample-diluent solution, step 150. Absorbance measurements of this sample-diluent solution in the liquid holder are made by spectrophotometry at wavelength $\lambda_b$ and at wavelength $\lambda_s$, step 160. The volume of the sample solution aliquot may then be calculated using the absorbance values obtained, step 180. Alternatively, steps 150 and 160 may be repeated one or more times, step 170, before calculating the volume of any one or more of the added aliquots not previously calculated, step 180. Further, steps 150 and 160 may be repeated one or more times after performing the step of calculating the volumes of any one or more of the added aliquots not previously calculated.

As described below, one embodiment of the hybrid absorbance volume calculation method contemplates determining the volumes of multiple sample solution aliquots which are mixed serially into successive sample-diluent solution mixtures. Regardless of whether the volume of only a single sample solution aliquot is being determined, or the volumes of multiple sample solution aliquots are being determined, however, the calculation of volumes of any single sample solution aliquot is based on the Beer-Lambert Law and occurs in the manner defined herein. Specifically, this calculation proceeds in two stages. First, the total volume of sample-diluent solution in the liquid holder after an $n^{th}$ delivery, $V_T(n)$, of a sample solution aliquot is calculated from the measured absorbance at wavelength $\lambda_b$ using the equation:

$$V_T(n) = V_b \left( \frac{A_b(0)}{A_b(n)} \right) \quad (8)$$

In this equation, $A_b(0)$ is the absorbance at the second wavelength $\lambda_b$ before the addition of the first sample solution aliquot and $A_b(n)$ is absorbance at wavelength $\lambda_b$ after the $n^{th}$ delivery. In other embodiments in which the sample solution does not have a Zero absorbance at wavelength $\lambda_b$, a different equation may be used to calculate the total volume of sample-diluent solution.

Next, the volume of the sample solution aliquot added at an $n^{th}$ addition, $V_s(n)$, is calculated using the measured absorbance value or absorbance values at wavelength $\lambda_s$ using the equation:

$$V_s(n) = \frac{V_T(n)A_s(n) - V_T(n-1)A_s(n-1)}{A_b(0)(\varepsilon_s C_s / \varepsilon_d C_d)} \quad (9)$$

The steps of adding sample solution aliquots, measuring the absorbances of that particular sample-diluent solution at wavelengths $\lambda_b$ and $\lambda_s$ and performing the calculations of equations (8) and (9) may be repeated as often as desired.

Variation in temperature of the diluent solution or the sample-diluent solution can cause variation in absorbance value measurement. In another embodiment of the hybrid absorbance volume calculation method, the temperatures of the diluent solution and the sample-diluent solution are measured immediately before absorbance values are measured for each of these solutions, and then a correction is applied in the calculation of sample aliquot volume. A description of the method of correction is presented in the Curtis '365 patent.

In one embodiment of the hybrid absorbance volume calculation method, the calculation of volume of any single sample solution aliquot, step 180, is performed by using the computer-executable software on the computer system 40.

In an alternative embodiment of the hybrid absorbance volume calculation method, the volume of the sample solution aliquot is calculated manually by the end-user. That is, in this embodiment, the volume of the sample solution aliquot is calculated without using the computer-executable software.

Figure 3:
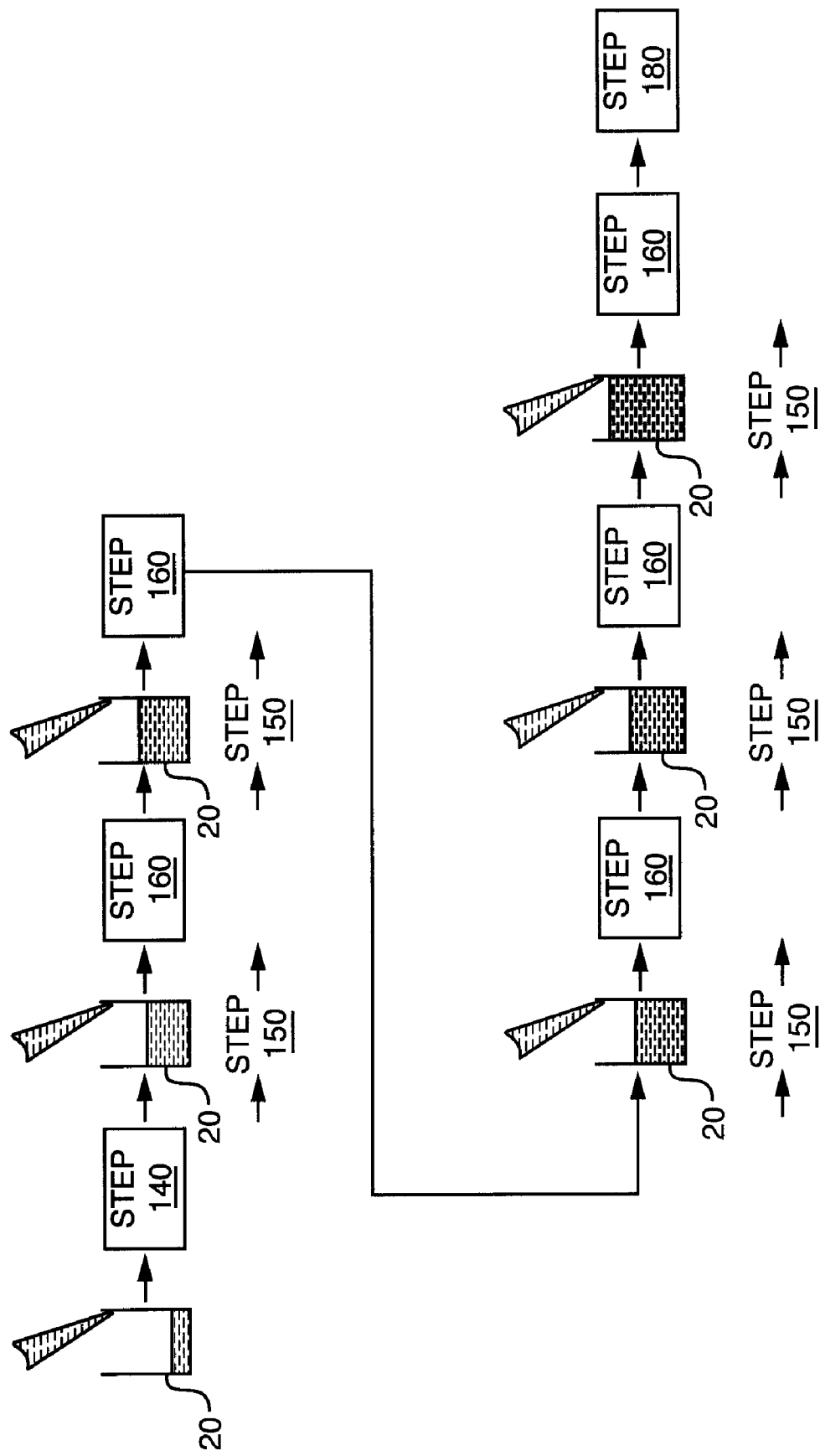
FIG. 3 is a flow diagram showing one embodiment of the hybrid absorbance volume calculation method.

In another embodiment of the hybrid absorbance volume calculation method, more than one sample solution aliquot is mixed into the diluent solution in the liquid holder, with absorbance measurements being made at wavelength $\lambda_b$ and at wavelength $\lambda_s$ after the addition of each sample solution aliquot. An example of this embodiment of the method, in which the aliquot measurement and calculation steps are repeated, is represented in FIG. 3. FIG. 3 shows five sample solution aliquots being added stepwise into the liquid holder prior to being measured at wavelength $\lambda_b$ and at wavelength $\lambda_s$, step 160 of FIG. 2 and FIG. 3. It is to be noted that the total number of sample solution aliquots which may be serially mixed into the liquid holder may be fewer or more than five.

While the calculation of the volume of any single sample solution aliquot, step 180, is shown in FIG. 3 as being performed after the final (fifth) aliquot addition, the calculation is not limited to being performed only after such final addition. Instead, the calculation may be performed at any time following the first instance of addition and may be performed multiple times. For example, the calculation may be performed after each aliquot addition.

Figure 4:
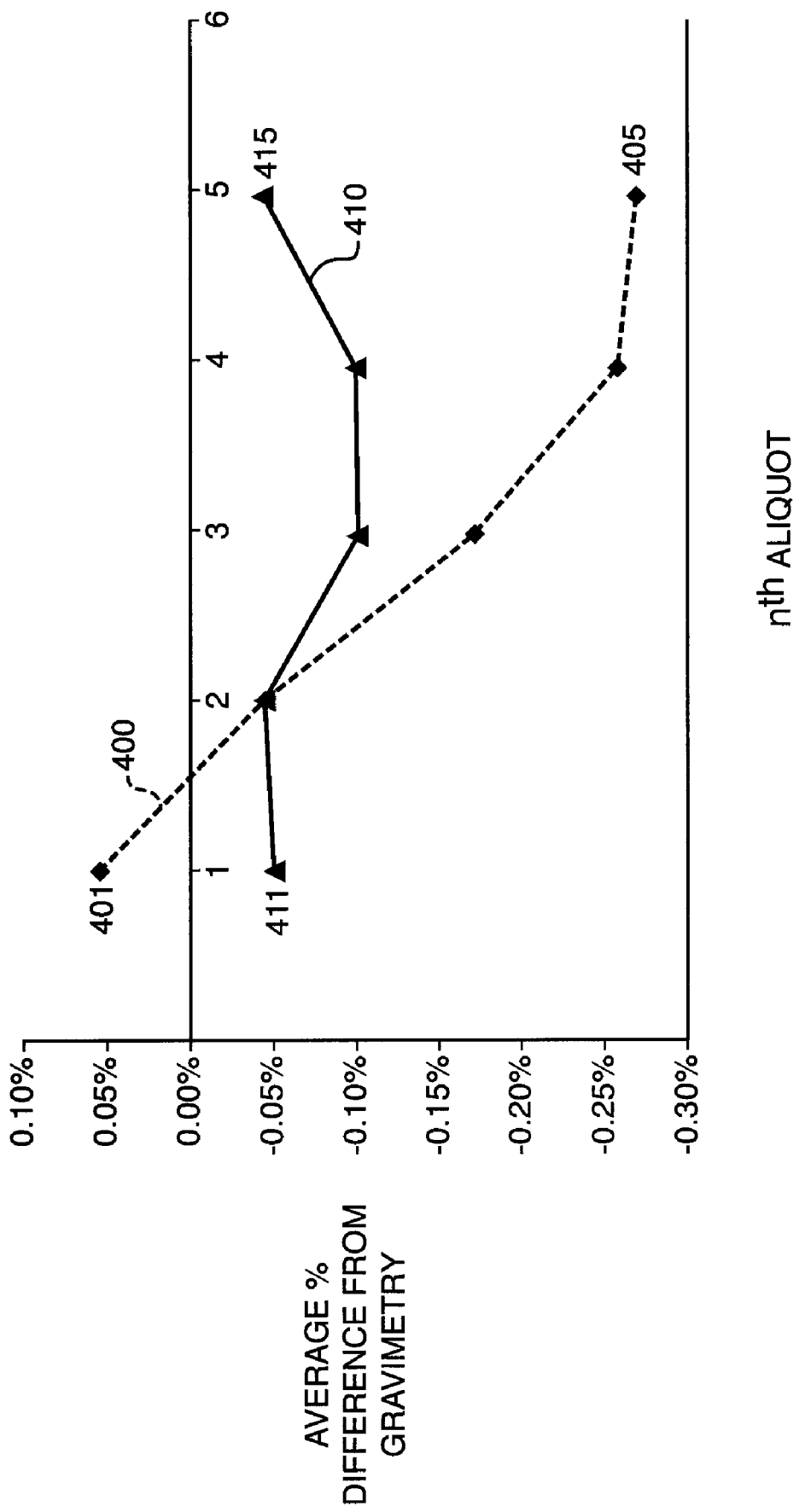
FIG. 4 is a graphical comparison of volumes calculated using the prior dye-addition method and volumes calculated using the hybrid absorbance volume calculation method, where both methods used the same absorbance data.

FIG. 4 shows data evaluated using the hybrid absorbance volume calculation method, which is precise and accurate and free of trending. Specifically, FIG. 4 shows a graphical comparison of data evaluated using the prior dye-addition method represented by curve 400, and the same data evaluated using the present hybrid absorbance volume calculation method represented by curve 410, both relative to gravimetry. Data obtained by performing gravimetric analysis is an appropriate standard with which to compare the performance of the hybrid absorbance volume calculation method to that of the dye-addition method because the volumes that were measured by gravimetric analysis, which specifically were 1000 μL, were large and therefore less susceptible to environmental conditions, such as evaporation, that might significantly skew volume determination. As FIG. 4 shows and as explained as follows, the volumes calculated with the dye-addition method trend away from the gravimetrically determined volumes, whereas the volumes calculated with the hybrid absorbance method do not display a trending deviation from gravimetry. The data evaluated with both methods was generated by first adding a known volume of diluent solution (which was made according to step 120 of FIG. 2) to a liquid holder, and then measuring the absorbance of the diluent solution in the liquid holder at wavelength $\lambda_b$ and at wavelength $\lambda_s$ (step 140 of FIG. 2). Next, one 1000 μL aliquot of sample solution (which was made according to step 110 of FIG. 2) was mixed into the diluent solution in the liquid holder (step 150 of FIG. 2), and the absorbance value of the resulting sample-diluent solution was measured at wavelength $\lambda_b$ and at wavelength $\lambda_s$ (step 160 of FIG. 2). The steps of mixing a single sample solution aliquot with diluent solution (step 150 of FIG. 2) and measuring the absorbance value of the resulting sample-diluent solutions at wavelength $\lambda_b$ and at wavelength $\lambda_s$ (step 160 of FIG. 2) after the addition of each aliquot, was repeated four more times (step 170 of FIG. 2), for a total of five times. The measured absorbance values at wavelengths $\lambda_b$ and $\lambda_s$ were then used to calculate the volume of sample solution dispensed for each aliquot using the hybrid absorbance method (step 180 of FIG. 2). Using aliquots of 1000 μL gave reliable gravimetric data (evaporation and other factors did not greatly affect the reading).

The absorbance data measured at wavelength $\lambda_b$ was also used to calculate the volume of sample solution dispensed for each aliquot using the prior dye-addition method. The resulting volumes from both methods were compared to gravimetry and the relative inaccuracies were plotted in the graph in FIG. 4.

Curve 410 in FIG. 4 represents an example of data evaluated using the hybrid absorbance volume calculation method, which is free of trending. Specifically, in FIG. 4, error seen in the dye-addition method curve 400 progressively becomes larger as sample solution aliquots are added to the liquid holder and measured; the calculated volume for the first aliquot reading point 401, has an error of +0.05% and the calculated volume for the fifth (final) aliquot reading point 405, has an error of −0.30%, which corresponds to an error range of 0.35%. Conversely, error seen in the data evaluated using the present hybrid absorbance volume calculation method does not become progressively larger as sample solution aliquots are added and measured, but instead volumes calculated remain relatively constant from aliquot to aliquot as was the case in the gravimetric data.

The first dye referred to herein may be any compound which selectively absorbs light, and the second dye referred to herein may be any other compound which selectively absorbs light, with the only limitation being that the first dye must have an extinction coefficient that allows the sample solution to have an absorbance value at a first wavelength which is different from the absorbance value at a second wavelength, and the second dye must have an extinction coefficient that allows the diluent solution to have an absorbance value at the first wavelength which is different from the absorbance value at the second wavelength. In a preferred embodiment of the hybrid absorbance volume calculation method, wherever the first dye and the second dye are added to a particular solution, absorbance measurements are not made using the solution until all dye material is fully dissolved into the solution. In another embodiment of the hybrid absorbance volume calculation method, wherever the first dye and the second dye are added to a particular solution, absorbance measurements are made using the solution before all dye material is fully dissolved into the solution. In this embodiment, a small amount of dye material may remain undissolved in the solution. In yet another embodiment of the hybrid absorbance volume calculation method, wherever the first dye and the second dye are added to a particular solution, none of the dye material is dissolved into the solution, but instead exists in the solution as undissolved particulate. For example, the undissolved particulate may be, but is not limited to being, in the form of small beads. Examples of compounds which may be used as the first dye and the second dye are presented in the Curtis '365 patent.

The liquid holder described herein may be any type of holder suitable for retaining liquid therein, such as a cuvette. A cuvette is best used, but is not limited to being used, when only one volume, or only a few volumes, are to be measured. For example, when calibrating one single-channel pipette, one typically would elect to measure only a few sample solution aliquots. Considerations for selecting a cuvette suitable for making absorbance measurements by spectrophotometry are described in the Curtis '365 patent and in the published Bradshaw et al. application.

Alternatively, the liquid holder may be the well of a multi-well plate. This embodiment permits multiple wells of a multi-well plate to be used simultaneously to determine the volumes of several sample solution aliquots. This would be particularly helpful, for example, for calibrating the channels of a multi-channel delivery device. However, this embodiment is not limited to being used to determine the volumes of several sample solution aliquots, as it could be used to determine only one volume of one sample solution aliquot. Considerations for selecting a liquid holder which is well suitable for making absorbance measurements by spectrophotometry are described in the published Bradshaw et al. application.

In another embodiment of the hybrid absorbance volume calculation method, absorbance measurements may be made without using a liquid holder suitable for use within a spectrophotometer. As examples, absorbance measurements may be made by using a probe connected to a spectrophotometer by a fiber optic cable, or solution absorbance values may be measured while the solution passes through a flow cell. It therefore is contemplated that any or all absorbance measurements made by following the hybrid absorbance volume calculation method may be performed by using any spectrophotometry-based means for making such measurements as would be recognized by one who is ordinarily skilled in the art.

The method of the present invention may be carried out using components of a volume determination kit. The kit preferably includes diluent solution sealed in a liquid holder and further includes instructions for conducting the hybrid absorbance volume calculation method of the present invention. In this embodiment, only the diluent solution is added to the liquid holder, and the liquid holder is sealed to prevent the diluent solution from evaporating or spilling. Sealing the liquid holder has at least one significant practical use. Namely, such sealing enables an entity having precisely and accurately calibrated dispensing equipment, such as a commercial manufacturer, to measure and ship a precisely and accurately measured volume of diluent solution in a liquid holder to an end-user having a delivery device in need of calibration, with minimal risk of loss of the diluent solution therein. Having such a precisely and accurately measured volume of diluent solution prepared by another is especially useful to any end-user lacking access to a delivery device which is known to be precisely and accurately calibrated.

In another embodiment, the kit containing the diluent solution in the sealed liquid holder and the instructions for conducting the hybrid absorbance volume calculation method of the present invention further includes the first dye. Inclusion of the first dye in the kit enables the entity manufacturing the kit to suitably select the first dye, with the goal of this selection being to remove a potential source of error in using the kit, which namely is the selection of an unsuitable first dye by the end-user.

In another embodiment, the kit containing the diluent solution in the sealed liquid holder and the instructions for conducting the hybrid absorbance volume calculation method of the present invention further includes the sample solution. Inclusion of the sample solution, which contains the first dye, in the kit enables the entity manufacturing the kit to supply a sample solution which it has deemed suitable. Having a suitable sample solution supplied in the kit would help the end-user avoid potential sources of error in using the kit, which are namely the selection of an unsuitable first dye (which is part of the sample solution) and the improper preparation of the sample solution by the end-user.

In another embodiment, the kit containing the diluent solution in the sealed liquid holder and the instructions for conducting the hybrid absorbance volume calculation method of the present invention further includes computer-executable software stored on a computer-readable medium, the computer-executable software being capable of calculating sample solution volume based upon spectrophotometric readings of an absorbance value at first wavelength $\lambda_s$, an absorbance value at second wavelength $\lambda_b$, a path length dimension of the liquid holder in which the readings are made, and if required, a correction applied to the absorbance readings to account for a deviation from the Beer-Lambert law.

In one embodiment of the invention, the computer-executable software includes computer-readable signals tangibly embodied on the computer-readable medium, where such signals define instructions for processing data obtained from the spectrophotometer. Such instructions may be written in any of a plurality of programming languages, for example, Java, XML, Visual Basic, C, or C++, Fortran, Pascal, Eiffel, BASIC, COBOL, and the like, or any of a variety of combinations thereof. The computer-readable medium on which such instructions preferably reside is to be compatible with the central processing unit of the computing system. Further, the steps of processing the data obtained from the spectrophotometer may be performed in alternative orders, in parallel and serially.

It is to be understood that various modifications may be made to the apparatus, the hybrid absorbance volume calculation method, and/or the kit without departing from the spirit and scope of the invention. For example, a sample solution which does not have a zero absorbance at one wavelength could be used. Also, the steps of the method may be performed in differing order, one or more steps may be omitted, and one or more steps may be replaced with alternative forms thereof. Accordingly, other embodiments are within the scope of the claims appended hereto.

What is claimed is:

1. A method for determining the volume of a liquid aliquot, comprising the steps of:
   a. making a sample solution by adding a first dye to a solvent, the first dye having an extinction coefficient such that the sample solution has an absorbance value at a first wavelength which is different from an absorbance value at a second wavelength, wherein the sample solution made includes no other dye;
   b. making a diluent solution by adding a second dye to a solvent, the second dye having an extinction coefficient such that the diluent solution has an absorbance value at the first wavelength which is different from an absorbance value at the second wavelength, wherein the second dye is different from the first dye and wherein the diluent solution made includes no other dye;
   c. measuring the absorbance value of a known volume of the diluent solution at the first wavelength and at the second wavelength;
   d. adding an aliquot of the sample solution containing the first dye only to the known volume of diluent solution of step (c) to make a sample-diluent solution;
   e. measuring the absorbance value of the sample-diluent solution of step (d) at the first wavelength and at the second wavelength; and
   f. calculating the volume of the aliquot of the sample solution by using the absorbance values measured in step (c) and step (e).

2. The method of claim 1 wherein after step (e) is performed, steps (d) and (e) are repeated successively at least one more time before step (f) is performed at least one time.

3. The method of claim 1 wherein after step (f) is performed, steps (d)-(f) are repeated successively n times, where n is greater than or equal to 1.

4. The method of claim 1 wherein step (f) is performed by using computer-executable software stored on a computer-readable medium, the computer-executable software being capable of calculating volume of a liquid sample solution aliquot based upon absorbance values measured by using the method.

5. The method of claim 1 wherein step (f) includes the step of calculating total volume using the equation:

$$V_T(n) = V_b\left(\frac{A_b(0)}{A_b(n)}\right).$$

6. The method of claim 5 wherein step (f) further includes the step of calculating the aliquot volume using the equation:

$$V_s(n) = \frac{V_T(n)A_s(n) - V_T(n-1)A_s(n-1)}{A_b(0)(\varepsilon_s C_s/\varepsilon_d C_d)}.$$

7. The method of claim 1 wherein the temperature of the diluent solution of step (c) is measured before step (c) is performed, and the temperature of the sample-diluent solution is measured before step (e) is performed.

8. The method of claim 7 wherein the temperature of either or both of the diluent solution and the sample-diluent solution are used in the calculation in step (f).

* * * * *